United States Patent [19]

Schwan

[11] 3,932,449

[45] Jan. 13, 1976

[54] 5-(P-DIMETHYLAMINOBENZYL) HYDANTOIN

[75] Inventor: Thomas J. Schwan, Norwich, N.Y.

[73] Assignee: Morton-Norwich Products, Inc., Norwich, N.Y.

[22] Filed: Oct. 9, 1973

[21] Appl. No.: 404,171

[52] U.S. Cl. ............................. 260/309.5; 424/273
[51] Int. Cl.² ......................................... C07D 49/32
[58] Field of Search ................................ 260/309.5

[56] References Cited
UNITED STATES PATENTS

| | | | |
|---|---|---|---|
| 2,759,002 | 8/1956 | Close | 260/309.5 |
| 3,032,581 | 5/1962 | Leonard | 260/309.5 X |
| 3,454,629 | 7/1969 | Daeniker | 260/309.5 |

OTHER PUBLICATIONS

Nitz et al., Arzneimitte-Forschung, No. 7, 7/'55, pp. 357–364.
C.A. 65: 13686f.
C.A. 54: 24678f.
C.A. 57–61, Accumulative 5738s.

*Primary Examiner*—Ethel G. Love
*Attorney, Agent, or Firm*—Anthony J. Franze

[57] ABSTRACT

The title compound is useful as an antidepressant.

1 Claim, No Drawings

5-(P-DIMETHYLAMINOBENZYL) HYDANTOIN

This invention is concerned with the chemical compound 5-(p-dimethylaminobenzyl)hydantoin. It has pharmacologic activity. When administered perorally to mice incrementally at one-half log intervals in a dose range of 1–30 mg/kg followed by an intraperitoneal injection of 35 mg/kg of tetrabenazine methane-sulfonate in normal saline, prevention of ptosis induced by said tetrabenazine is achieved. The antidepressant effect of the compound of this invention exemplified by its antagonism to tetrabenzaine makes it a valuable pharmacologic agent.

The method for preparing the compound of this invention is readily carried out. It is illustrated by the following example:

A mixture of 69.3 g (0.30 mole) of 5-(p-dimethylaminobenzylidene)-hydantoin, 600 ml 1 N KOH and 15 g wet Raney Nickel was shaken with hydrogen until the theoretical quantity had been consumed (28 hr). The catalyst was washed with 2 × 100 ml 1 N KOH and the filtrate and combined washings were acidified with glacial acetic acid. The white solid was filtered through a medium sintered glass funnel and air dried to give 60 g of the crude product. Recrystallization from methanol gave 35 g (50%) of the product, m.p. 180°–186°.

Anal. Calcd. for $C_{12}H_{15}N_3O_2$: C, 61.78; H, 6.48; N, 18.02. Found: C, 61.79; H, 6.45; N, 18.10.

What is claimed is:

1. The compound 5-(p-dimethylaminobenzyl)hydantoin.

* * * * *